United States Patent [19]
Bieger et al.

[11] Patent Number: 5,938,608
[45] Date of Patent: Aug. 17, 1999

[54] THERAPY APPARATUS FOR CARRYING OUT TREATMENT WITH FOCUSED ULTRASOUND

[75] Inventors: Johannes Bieger, Möhrendorf; Ulrich Schätzle, Röttenbach; Erhard Schmidt; Siegfried Schneider, both of Erlangen, all of Germany

[73] Assignee: Siemens Aktiengesellschaft, Munich, Germany

[21] Appl. No.: 08/894,980

[22] PCT Filed: Feb. 19, 1996

[86] PCT No.: PCT/DE96/00254

§ 371 Date: Sep. 2, 1997

§ 102(e) Date: Sep. 2, 1997

[87] PCT Pub. No.: WO96/27408

PCT Pub. Date: Sep. 12, 1996

[30] Foreign Application Priority Data

Mar. 3, 1995 [DE] Germany ............... 195 07 478

[51] Int. Cl.⁶ .................................................. A61B 17/22
[52] U.S. Cl. ................................................ 600/439; 601/4
[58] Field of Search ........................ 600/439; 601/2–4

[56] References Cited

U.S. PATENT DOCUMENTS

| | | |
|---|---|---|
| 4,526,168 | 7/1985 | Hassler et al. . |
| 4,586,512 | 5/1986 | Do-huu et al. . |
| 4,865,042 | 9/1989 | Umemura et al. ............... 600/439 |
| 4,893,624 | 1/1990 | Lele . |
| 4,936,303 | 6/1990 | Detwiler et al. ............... 601/4 |
| 4,938,217 | 7/1990 | Lele . |
| 4,957,099 | 9/1990 | Hassler . |
| 5,065,762 | 11/1991 | Ifflaender et al. . |
| 5,111,805 | 5/1992 | Jaggy et al. . |
| 5,207,215 | 5/1993 | Rattner et al. . |
| 5,243,985 | 9/1993 | Aida et al. ............... 600/439 |
| 5,247,924 | 9/1993 | Suzuki et al. ............... 601/4 |
| 5,251,630 | 10/1993 | Rattner ............... 600/439 |
| 5,279,282 | 1/1994 | Oppelt ............... 601/4 |
| 5,305,731 | 4/1994 | Buchholtz ............... 601/4 |
| 5,727,556 | 3/1998 | Weth et al. ............... 600/439 |

FOREIGN PATENT DOCUMENTS

| | | |
|---|---|---|
| 0 310 380 | 4/1989 | European Pat. Off. . |
| 0 367 117 | 5/1990 | European Pat. Off. . |
| 0 214 782 | 6/1992 | European Pat. Off. . |

*Primary Examiner*—Brian L. Casler
*Attorney, Agent, or Firm*—Hill & Simpson

[57] ABSTRACT

The invention is directed to a therapy apparatus for treatment with focussed ultrasound, comprising a cooled ultrasound source (1) implemented as phased array and a preceding acoustic lens (6). The ultrasound source (1) also comprises a base plate (3) arranged between the lens (6) and the ultrasound source (1) on whose side facing away from the lens (6) the ultrasound transducer elements ($2_1$ through $2_6$) of the phased array are attached, whereby the base plate (3) is composed of a material with good thermal conductivity, whereby an ultrasound-conductive coolant that adjoins that side of the base plate (3) facing toward the lens (6) is situated between the lens (6) and the ultrasound source (1), whereby the base plate (3), at least in the region of the ultrasound transducer elements ($2_1$ through $2_6$), comprises a thickness that is equal to an odd-numbered multiple of a quarter of the wavelength of the ultrasound in the material of the base plate (3).

18 Claims, 7 Drawing Sheets

THERAPY APPARATUS FOR CARRYING OUT TREATMENT WITH FOCUSED ULTRASOUND

BACKGROUND OF THE INVENTION

1. Field of the Invention

The invention is directed to a therapy apparatus for treatment with focussed ultrasound, comprising a cooled ultrasound source implemented as phased array and a preceding acoustic lens.

2. Description of the Prior Art

A therapy apparatus of the above type is utilized for treating both benign as well as malignant tissue modifications. Temperatures in the range from 40 through 100° C. can be generated in the focus during the treatment, whereby the temperature is selected dependent on the clinical picture to be respectively treated.

The employment of phased arrays for ultrasound therapy is disclosed by German OS 31 19 295 The advantage of employing phased arrays is comprised therein that the focus zone of the ultrasound can be displaced by suitable drive of the phased array without requiring the is displacement of the ultrasound source relative to the subject to be treated.

In order to reduce the number of ultrasound transducer elements of the phased array required in order to enable a specific displacement of the focus zone, a prefocussing with an acoustic lens is provided in European Application -0 214 782, which is directed to a therapy apparatus of the species initially cited. In order to save installation space, the acoustic lens is implemented as a Fresnel lens. At the same time, the Fresnel lens serves as carrier for the ultrasound transducer elements of the phased array, these being attached to the back side of the Fresnel lens facing away from the focus zone. At its front side, the Fresnel lens, which also acts as an acoustic matching layer, is provided with a further acoustic matching layer.

For heat elimination, the Fresnel lens is provided with a cooling channel in the region of its outer edge. Since the cooling channel can only be provided in the region of the edge of the Fresnel lens, the cooling is not very effective. Added thereto is that the realization of a Fresnel lens containing a cooling channel involves rather considerable outlay. The manufacture of the matching layer applied to the Fresnel lens also involves high outlay.

U.S. Pat. No. 4,936,303 also discloses a therapy apparatus with an ultrasound source and a preceding acoustic lens. For cooling the ultrasound source, an ultrasound-conductive coolant adjoining that side of the ultrasound source facing toward the lens is located between the lens and the ultrasound source.

U.S. Pat. No. 4,586,512 also discloses a therapy apparatus for treatment with focussed ultrasound, wherein an ultrasound source executed as phased array is cooled with an adjacent coolant. An acoustic lens is not provided.

SUMMARY OF THE INVENTION

An object of the present invention is to provide a therapy apparatus of the type initially described such that an effective cooling of the ultrasound source and a good impedance matching of the ultrasound source are assured in a simple way.

This object is inventively achieved in an ultrasound source having a base plate arranged between the lens and the ultrasound source on whose side facing away from the lens the ultrasound transducer elements are applied, whereby the base plate is composed of a material having good thermal conductivity, whereby a coolant that conducts ultrasound waves and adjoins the side of the base plate facing toward the lens is located between the lens and the ultrasound source, whereby the base plate comprises a thickness, at least in the region of the ultrasound transducer elements, that is equal to an odd-numbered multiple of a quarter of the wavelength of the ultrasound in the material of the base plate and exhibits an acoustic impedance in the region of the ultrasound transducer elements that lies on the order of magnitude of $10^7$ kg/(m$^2$s). Since a base plate separate from the lens is provided for the ultrasound transducer elements of the phased array, the ultrasound transducer elements being attached to the side thereof facing away from the lens, and since a coolant is adjacent at the other side of the base plate, which has good thermal conductivity, a good cooling of the ultrasound source is assured even without a cooling channel. As a result of the fact that the base plate comprises a thickness in the region of the ultrasound transducer elements that is equal to an odd-numbered multiple of a quarter of the wavelength of the ultrasound waves in the material of the base plate, this acts as a resonance matching layer and thus assures an optimum sound impedance matching of the material of the ultrasound transducer elements to the coolant through which the generated ultrasound proceeds to the lens. A second matching layer is thus not required; this, moreover, is also undesirable in view of the cooling of the ultrasound source since it represents a thermal insulation. What is to be understood by a material having good thermal conductivity in conjunction of the base plate is a material whose coefficient of thermal conductivity is at least equal to 10 W/(m° K), i.e. that lies in the range typical of metals.

For instances wherein an especially good cooling effect is required, it is provided in a version of the invention that the space between the lens and the base plate has coolant flowing through it that, in one embodiment of the invention, can flow through a cooling unit in a circulation, an even more improved cooling effect being thereby achieved.

When the ultrasound source generates periodic ultrasound, the acoustic lens according to one version of the invention is implemented as a Fresnel lens for the sake of a small space requirement and low attenuation losses. As used herein, a Fresnel lens means a lens divided into a plurality of zones, whereby a phase shift that is equal to a whole multiple of the wavelength of the acoustic waves in the medium into which the acoustic waves enter from the Fresnel lens is present between the acoustic waves emerging from neighboring lens zones.

When, according to one version of the invention, the phased array is implemented as annular array with annular ultrasound transducer elements, there is the possibility of displacing the focus zone of the ultrasound along the middle axis of the ultrasound source by suitable drive of the phased array.

When the annular ultrasound transducer elements are arranged congruent with the annular zones of the Fresnel lens, the advantage derives that errors with respect to the Fresnel transitions, for example due to manufacturing imprecisions, can be electronically corrected. When the ultrasound transducer elements respectively have the same area, the advantage derives that the load impedance of the ultrasound transducer elements remains constant and the channels of the electronic control means of the phased array can be identically constructed for the individual ultrasound transducer elements.

According to a preferred embodiment of the invention, the phased array is implemented as 2D array. This offers the advantage that the focus zone can be spatially displaced. When regions are to be preferably treated that exhibit different thicknesses measured in different directions transversely to the middle axis of the 2D array, it can be expedient according to one embodiment of the invention when, correspondingly, the number of ultrasound transducer elements per length unit differs in the 2B array measured in different directions transversely to the middle axis of the 2D array.

A further embodiment of the invention provides that the phased array is implemented as linear array and is pivotable around its longitudinal axis or, respectively, an axis proceeding essentially parallel thereto and/or is adjustable at least essentially transversely to the direction of its longitudinal axis. Such a structure of the therapy apparatus is particularly advantageous when oblong regions are preferably to be treated or endoluminal access paths are used.

In order to be able to displace the focus zone of the ultrasound beyond the displacement possible as a result of fashioning the ultrasound source as phased array, it is provided according to a version of the invention that the ultrasound source and the lens are suspended cardanically swivellable in common.

A version of the invention provides that the therapy apparatus contains an ultrasound locating means. Even though there is basically the possibility of using the ultrasound source itself for locating purposes, it is expedient for the sake of a good image quality to provide a separate diagnostic ultrasound transducer according to an embodiment of the invention. This preferably extends through an opening provided in the lens and the ultrasound source and can be aligned such that the body region containing the focus zone of the ultrasound can be imaged in an ultrasound image. When a focussing of the ultrasound emanating from the diagnostic ultrasound transducer as also desired, the opening does not extend through the lens. When the diagnostic ultrasound transducer is placed onto the ultrasound source, an opening in the ultrasound source is not required.

Another preferred embodiment provides that the ultrasound source and the lens comprise an X-ray-transparent region. There is then the possibility of locating a region to be treated on the basis of an X-ray locating means through the X-ray-transparent region of ultrasound source and lens.

An especially preferred embodiment of the invention provides that an opening into which the diagnostic ultrasound transducer or an X-ray-transparent tube can be introduced extends through the ultrasound source and through the lens as swell under certain circumstances.

Exemplary embodiments of the invention are shown in the attached

DESCRIPTION OF THE PREFERRED EMBODIMENTS

Figure 1:
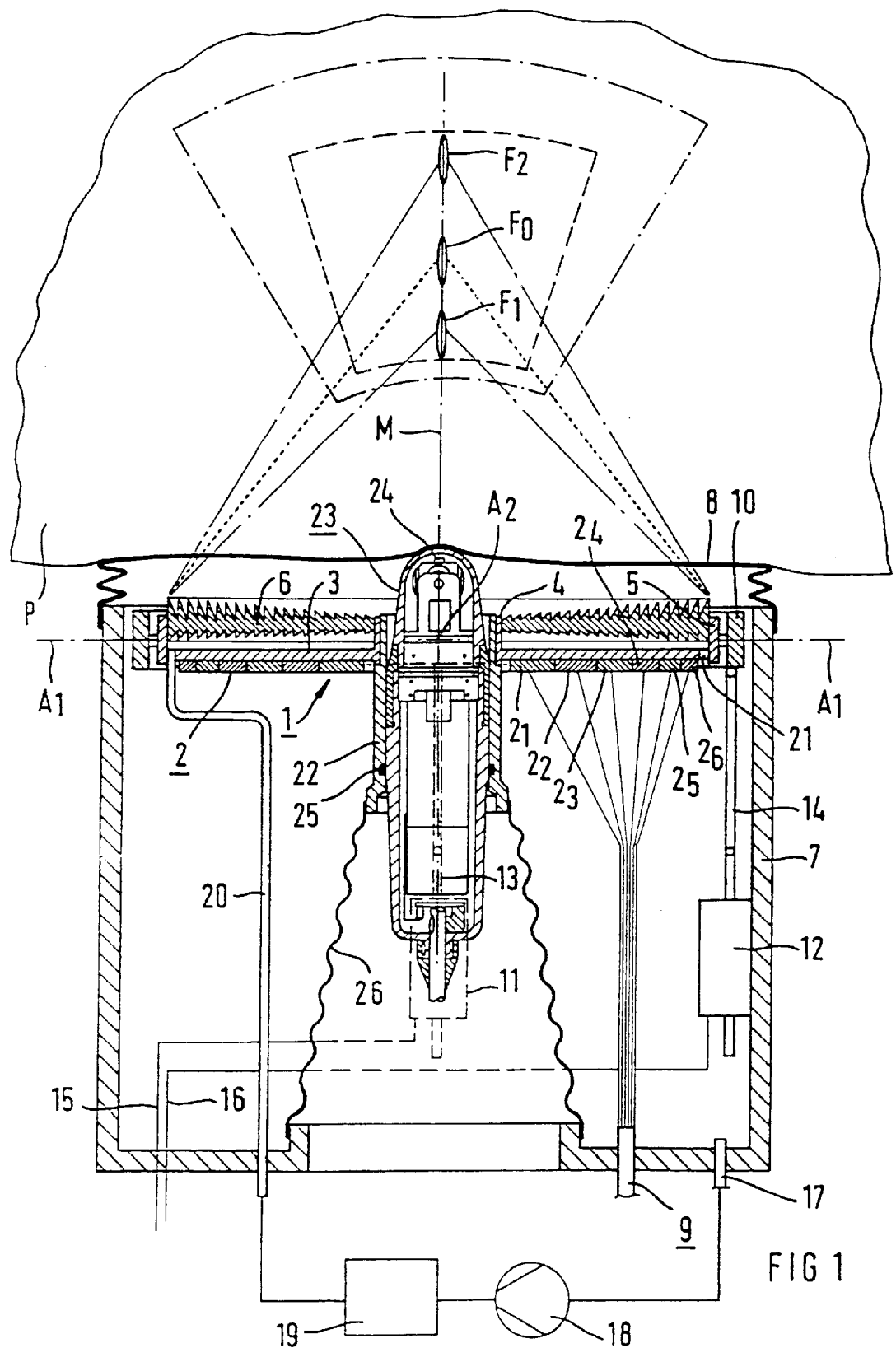
FIG. 1 is a longitudinal sectional view of a therapy apratus constructed in accordance with the principles of the present invention.
Figure 2:
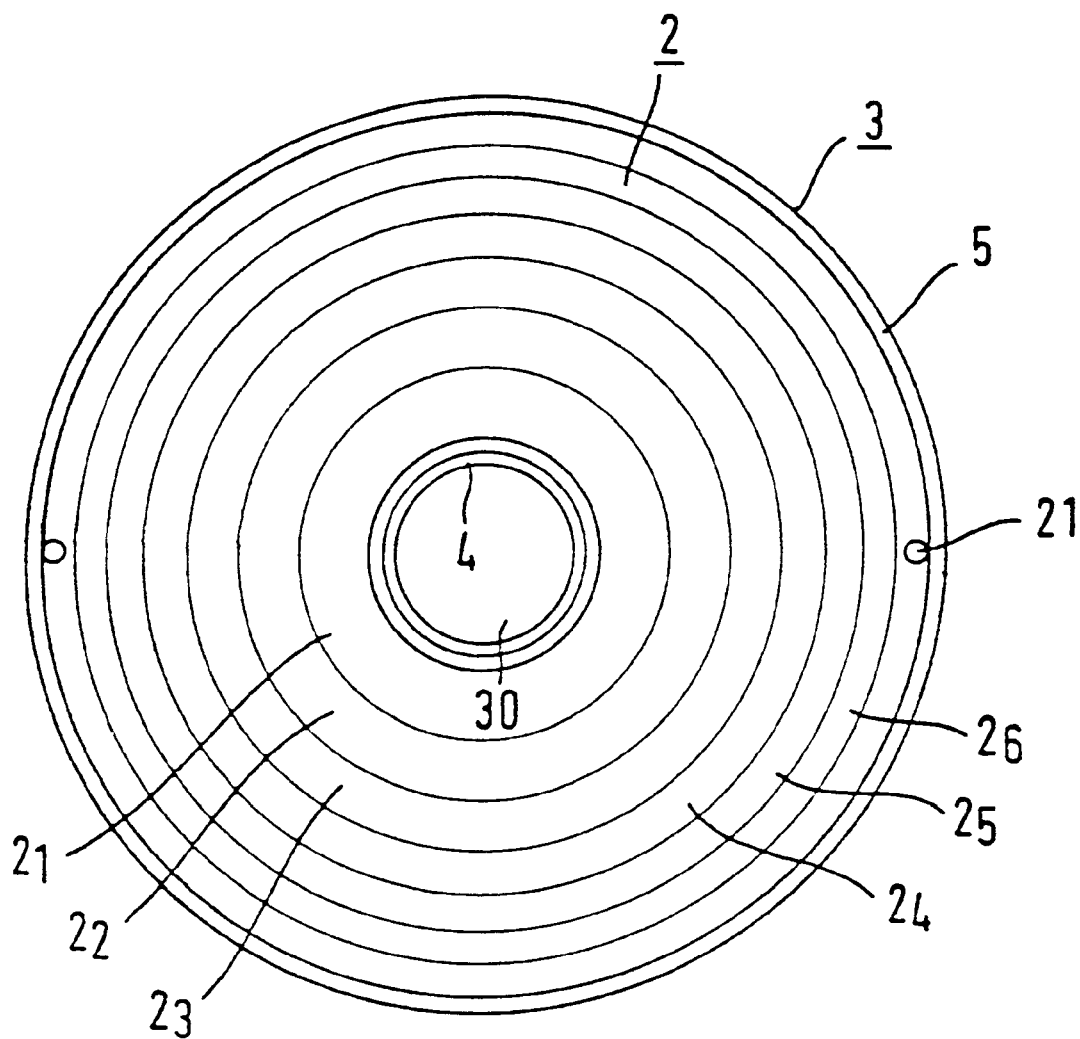
FIG. 2 shows a detail of the apparatus of FIG. 1.

The therapy apparatus according to FIGS. 1 and 2 contains a therapeutic ultrasound source referenced 1 overall. This contains six annular ultrasound transducer elements $2_1$ through $2_6$ that are secured to the one side of a carrier 3 forming a base plate. The carrier 3 is composed of a light metal, for example aluminum or magnesium.

The carrier 3 also has an essentially annular shape and comprises a flange 4 or, respectively, 5 both at its inner as well as at its outer circumferential edge. An acoustic lens implemented as Fresnel lens, namely a positive lens 6, is introduced between these. For reasons of clarity, the circumferential edges are only shown with respect to the outermost annular lens zone of the Fresnel lens in FIG. 1.

The ultrasound source 1 is accepted in a pot-shaped housing 7 that has its application end closed by a coupling membrane 8. The housing 7 is filled with a fluid, for example water, suitable as acoustic propagation medium for the ultrasound. The corresponding shading is not entered for reasons of clarity. The therapy apparatus is pressed against the body surface of a patient P to be treated with the coupling membrane 8 in the way shown in FIG. 1 in order to assure a good acoustic coupling for introducing the ultrasound emanating from the ultrasound source 1 into the body of the patient P. The space located between the positive lens 6 and the carrier 3 is also filled with the acoustic propagation medium. This assures a good cooling of the carrier 3 that absorbs a part of the waste heat arising during operation of the ultrasound source I and outputs it to the acoustic propagation medium, which thus acts as coolant at the same time.

The annular ultrasound transducer elements $2_1$ through $2_6$ form a phased array implemented as annular array 2. This is connected to a traditional drive means (not shown) via a multi-lead cable referenced 9 overall.

When the ultrasound transducer elements $2_1$ through $2_6$ of the phased array are driven conphasally, i.e. without phase shifts between the drive signals supplied to the individual ultrasound transducer elements $2_1$ through $2_6$, the emitted ultrasound is focussed onto a focus zone referenced $F_0$ in FIG. 1 that lies on the middle axis M of the ultrasound source 1. The focus zone can be displaced along the middle axis M between the two limit positions $F_1$ and $F_2$ by a suitably phase-offset drive of the ultrasound transducer elements $2_1$ through $2_6$.

The thickness of the ultrasound transducer elements is dimensioned such in a known way that resonance is present at the frequency with which the drive means drives the ultrasound source 1. The drive, moreover, ensues such that either continuous sound of a constant frequency or ultrasound pulses are generated whose length respectively covers a plurality of cycles of the constant-frequency signal in view of the fact that a Fresnel lens is provided as positive lens 6. The constant frequency is selected taking the frequency for which the Fresnel lens is designed into consideration.

In order to be able to shift the focus zone within a region indicated in broken lines in FIG. 1 that is rotational-symmetrical relative to the middle axis M and has a conical generated surface and two concentric, spherical end faces, the ultrasound source 1 together with the positive lens 6 is suspended cardanically swivellable in the housing 7. To that end, the carrier 3 is connected to a ring 10 swivellable around a first axis $A_1$ lying in the plane of the drawing of FIG. 1, said ring 10 being in turn connected to the housing 7 swivellable around an axis $A_2$ residing at a right angle to the plane of the drawing of FIG. 1.

In order to be able to undertake the cardanic adjustment by motor, two linear drives 11 and 12—which can thereby by electrical, pneumatic or hydraulic linear motors—are connected to the ring 10 or, respectively, the carrier 3 via articulated rods 13 or, respectively, 14. In a schematically indicated way, the linear drives 11, 12 are connected via lines 15, 16 to a control device that is not shown in FIG. 1.

In order to achieve an improved cooling effect, a cooling circulation path is provided for the acoustic propagation medium. To that end, the acoustic propagation medium is conducted with a pump 18 from the housing 7 via a first fluid conduit 17 through a cooling unit 19 and is conducted back into the housing via a second flexible fluid conduit 20 that discharges into the interspace between the carrier 3 and the positive lens 6. The acoustic propagation medium flows out again from the interspace located between the carrier 3 and the positive lens 6 through an opening 21 that lies diametrically opposite the discharge point of the fluid conduit 20.

In the region of the ultrasound transducer elements $2_1$ through $2_6$, the carrier 3 comprises a thickness d that is equal to an odd-numbered multiple of a quarter of the wavelength of the ultrasound in the material of the carrier 3 (for example, aluminum with a speed of sound of 6,320 m/s or magnesium with a speed of sound of 5,790 m/s). Since the material of the carrier—at least in the region of the ultrasound transducer elements $2_1$ through $2_6$—exhibits an acoustic impedance on the order of magnitude of $10^7$ kg/(m$^2$s) (for example, aluminum with an acoustic impedance of $17.1 \cdot 10^6$ kg/(m$^2$s) or magnesium with an acoustic impedance of $10.1 \cdot 10^6$ kg/(m$^2$s)), the carrier 3 acts as resonance matching layer that assures an optimum acoustic impedance matching of the piezoelectric material of the ultrasound transducer elements $2_1$ through $2_6$ (for example, PZ 27 with an acoustic impedance of $35 \cdot 10^6$ kg/(m$^2$s)) to the liquid (for example, water with an acoustic impedance of $1.5 \cdot 10^6$ kg/(m$^2$s)) provided as acoustic propagation medium.

An ultrasound applicator 23 that contains a diagnostic ultrasound transducer 24 and belongs to an ultrasound locating means is introduced in a tubular component 22 introduced into the inner flange 4 of the carrier 3. The arrangement is thereby undertaken such that ultrasound tomograms of a body slice of the patient P containing the middle axis M can be generated with the ultrasound applicator.

In order to prevent the acoustic propagation medium from emerging from the housing 7, a seal 25 is arranged, on the one hand, between the ultrasound applicator 23 and the tubular component part 22; on the other hand, the free end of the tubular component part 22 is connected fluid-tight via an accordion bellows 26 to the inner edge of the floor of the housing 7, which comprises an opening. The accordion bellows is provided in view of the cardanic swivel of the ultrasound source 1. If such a swivel of the ultrasound source 1 is not provided or is only provided to a limited extent, an accordion bellows seal can be provided in the region of the Cardan ring 10 instead of the accordion bellows 26. The part of the housing 7 facing away from the focus would then be free of fluid and the overall weight would be lower.

The region portrayed in the ultrasound tomogram is at least so big that the entire region within which the focus zone of the ultrasound can be displaced is imaged. When the ultrasound applicator is a matter of a sector scanner, the region that can be imaged is schematically indicated dot-dashed in FIG. 1.

In a known way, the ultrasound locating means comprises means that mix a mark corresponding to the momentary position of the focus zone of the ultrasound into the respectively generated ultrasound image. To that end and in a known way, the control means for the ultrasound source 1 supplies the ultrasound locating means with a signal corresponding to the momentarily set position of the focus zone and the control device for the linear drives 11, 12 supplies signals with respect to the spatial alignment of the ultrasound source 1.

In a known way that is not shown, moreover, it can be provided that the ultrasound applicator is rotatable around the middle axis M.

For the implementation of a treatment, one proceeds such that, with the assistance of the ultrasound locating means, the therapy device is first aligned such relative to the body of the patient that the region to be treated appears in the ultrasound tomogram; by pivoting the ultrasound source 1 and by adjusting the position of the focus zone on the middle axis M of the ultrasound source, the mark indicating the position of the focus zone is then brought into coincidence with the region to be treated. Following thereupon, the ultrasound source 1 is activated to output ultrasound in a way suitable for the respective therapy.

Given the ultrasound source 1 according to FIGS. 1 and 2, the width of the ultrasound transducer elements $2_1$ through $2_6$ increases from the inside to the outside, namely such that the end faces of the ultrasound transducer elements $2_1$ through $2_6$ respectively exhibit the same area content.

Figure 3:
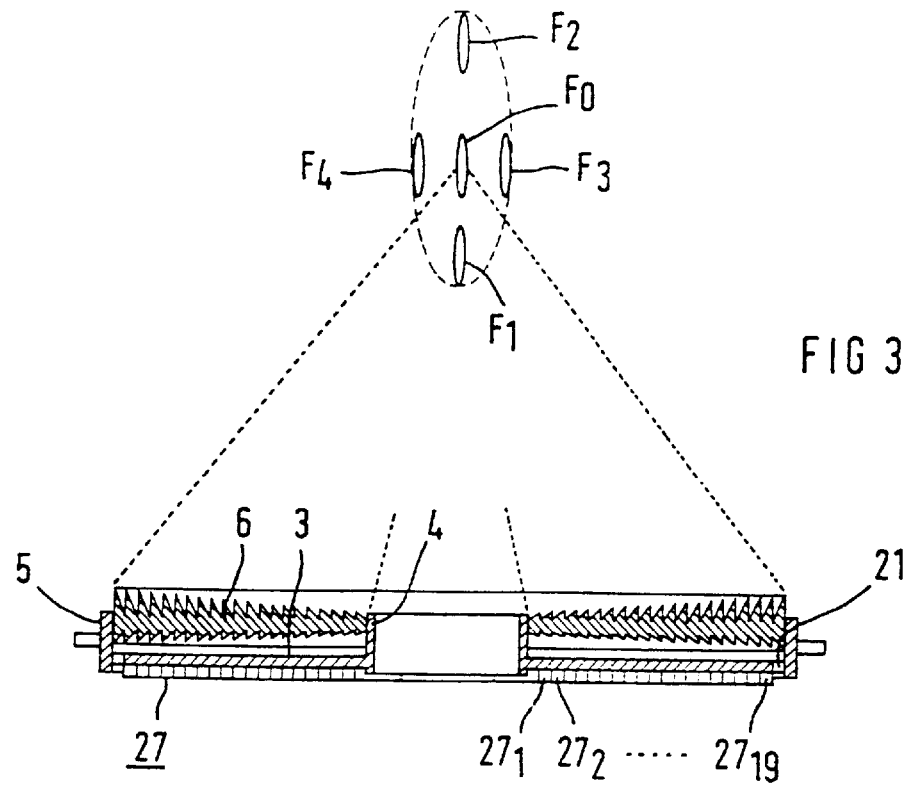
FIG. 3 is a longitudinal section through the ultrasound source and through the lens in a further embodiment of a therapy apparatus of the invention.
Figure 4:
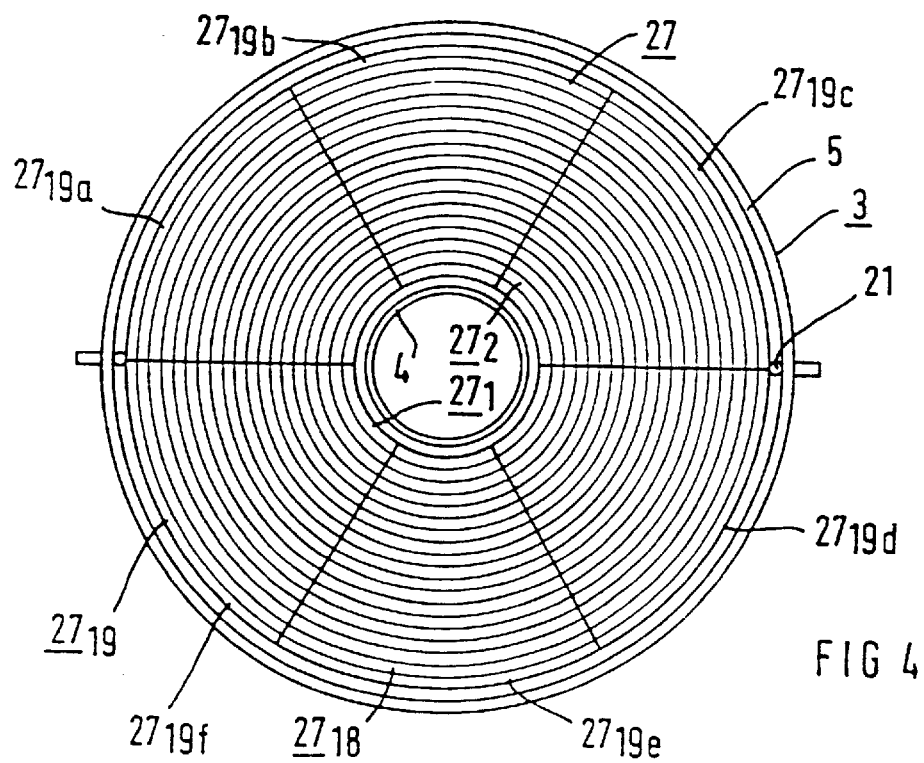
FIG. 4 shows a view of a detail of the apparatus of FIG. 3.

By contrast thereto, the ultrasound transducer elements $27_1$ through $27_{19}$ in the ultrasound source 1 according to FIGS. 3 and 4 likewise fashioned as annular array 27 exhibit the respectively same width. The width of the ultrasound transducer elements $27_1$ through $27_{19}$ is thereby selected such that they are arranged congruent with the annular zones of the positive lens 6, which is again fashioned as Fresnel lens.

In the exemplary embodiment according to FIGS. 3 and 4, the annular ultrasound transducer elements $27_1$ through $27_{19}$ are segmented such that segments $27_{1a}$ through $27_{19f}$ that are respectively 60° wide derive. Since a 2D array is present because of the segmentation, the focus zone can thus be displaced not only along the middle axis M of the ultrasound source 1 as in the exemplary embodiment according to FIGS. 1 and 2. On the contrary, a displacement transversely to the middle axis M is also possible (see the positions $F_3$ and $F_4$ additionally entered in FIG. 3 by way of example), namely within a rotation-elliptical region indicated in FIG. 3. It is self-evident that, for displacing the focus zone transversely to the middle axis M, the [. . . ] respectively [. . . ] to an ultrasound transducer element $27_1$ through $27_{19}$—let the segments $27_{19a}$ through $27_{19f}$ provided with reference characters in FIG. 4 be cited only by way of example—must be driven with drive signals that are offset in phase relative to one another.

Figure 5:
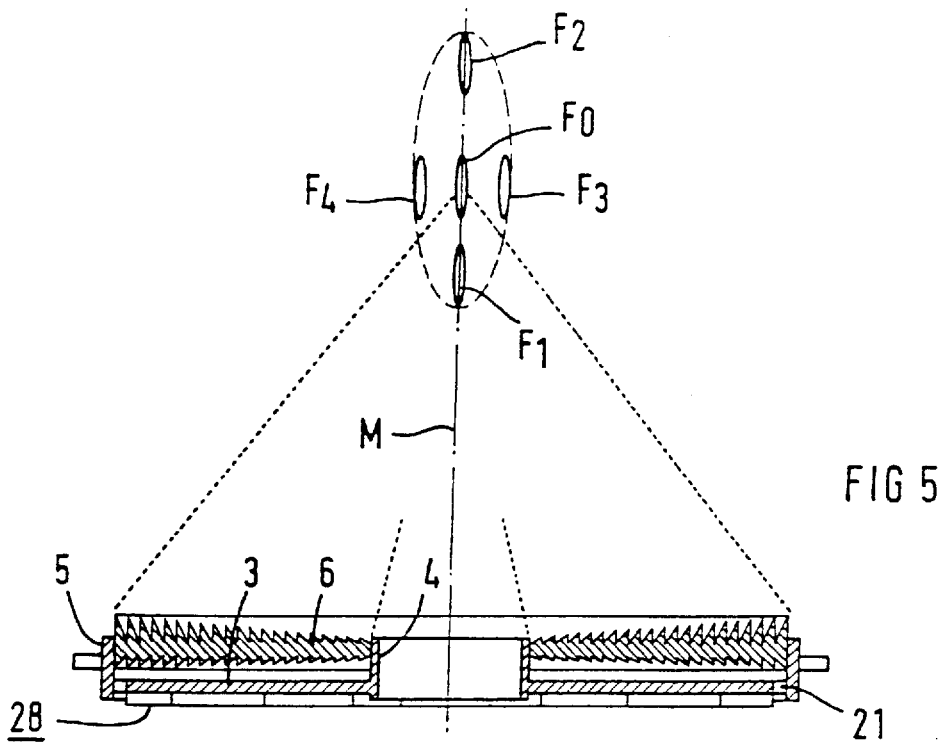
FIGS. 5 and 6 show a further embodiment of a therapy apparatus of the invention in a presentation analogous to FIGS. 3 and 4.
Figure 6:
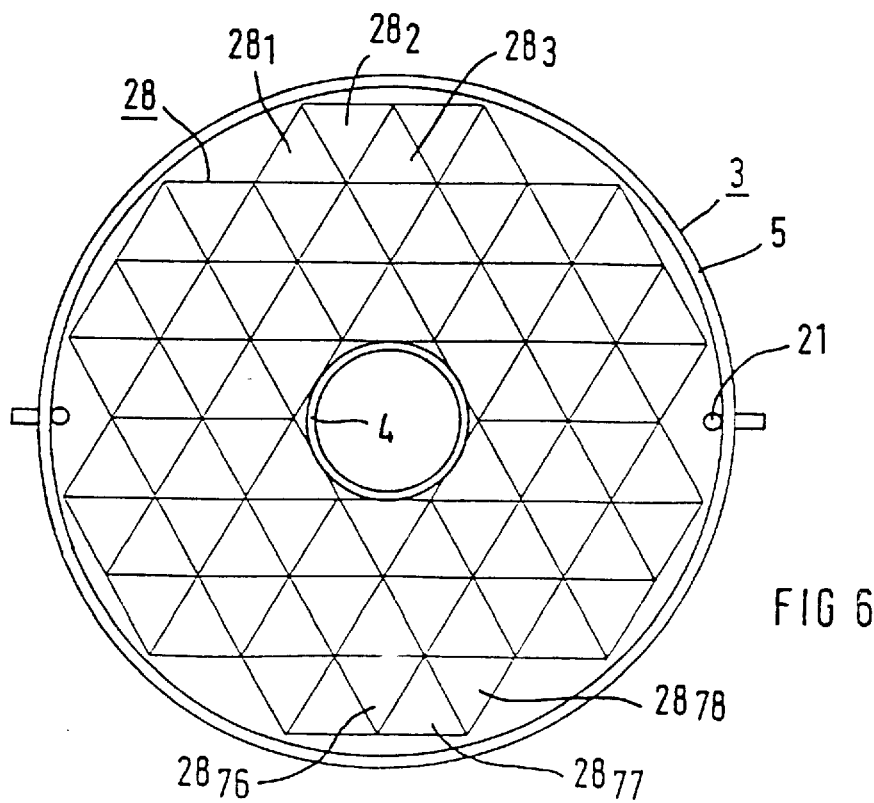

The ultrasound source 1 of the exemplary embodiment according to FIGS. 5 and 6 is also implemented as 2D array 28. It contains a total of 78 ultrasound transducer elements $28_1$ through $28_{78}$ that are attached mosaic-like to the carrier 3. Since the ultrasound transducer elements $28_1$ through $28_{78}$ are a matter of flat prisms with the crossection of an equilateral triangle, the focus zone of the ultrasound, as a result of the mosaic-like arrangement of the ultrasound transducer elements $28_1$ through $28_{78}$, is displaceable within an approximately rotation-elliptical region (see the positions of the focus zone $F_0$ through $F_4$ entered in FIG. 5), as in the case of the above-described exemplary embodiment.

Figure 7:
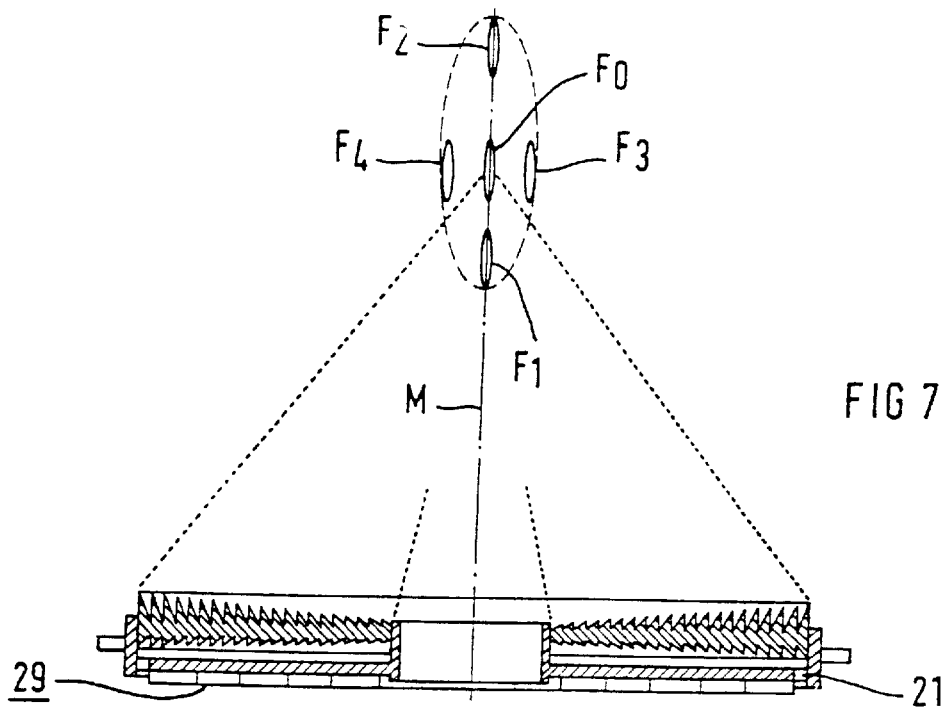
FIGS. 7, and 8 show a further version of a therapy apparatus of the invention in a presentation analogous to FIGS. 3 and 4.
Figure 8:
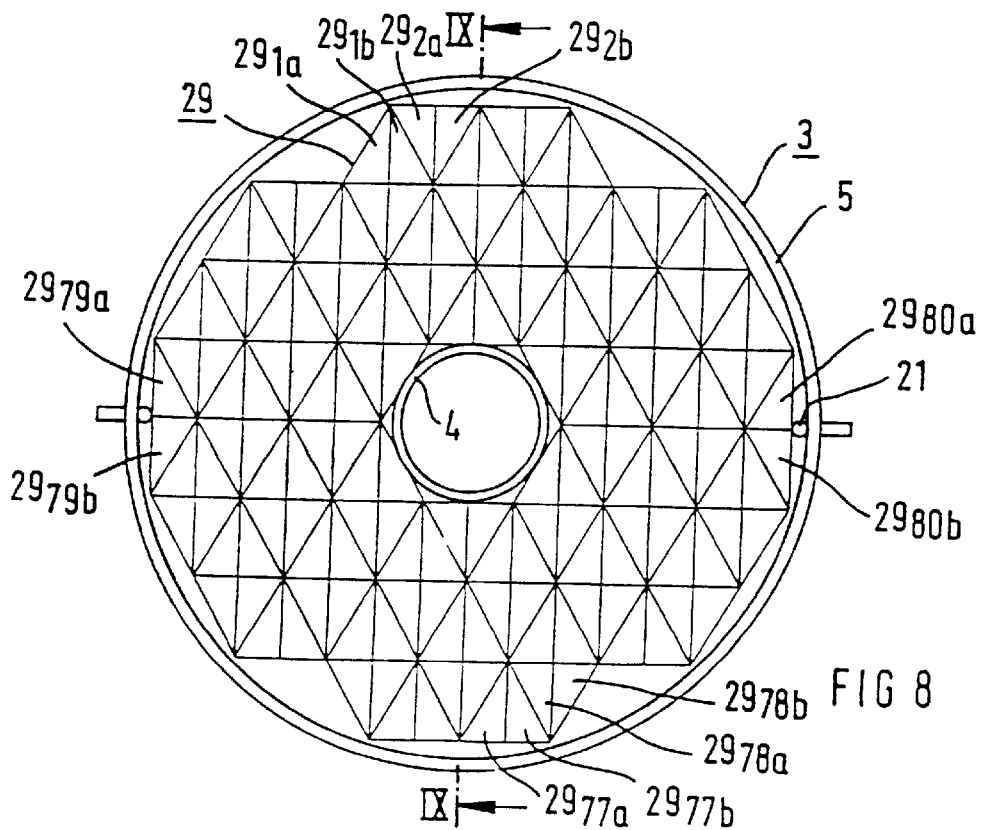
Figure 9:
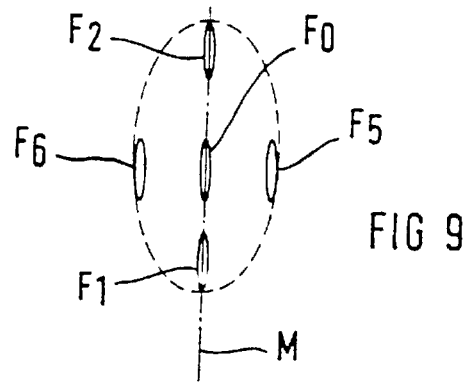
FIG. 9 is section through the focus zone of the therapy apparatus of the embodiment of FIGS. 7 and 8. taken along line IX—IX in FIG. 8.

The 2D array 29 of the exemplary embodiment according to FIGS. 7 through 9 differs from that described above in that the ultrasound transducer elements are divided again such that they exhibit the shape of flat prisms with the crossection of a right triangle, so that ultrasound transducer elements $29_{1a}$ through $29_{78b}$ are present. In addition, there is also room on the carrier 3 for ultrasound transducer elements $29_{79a}$ through $29_{80b}$. As a result of the further division of the ultrasound transducer elements, the number of ultrasound transducer elements per length unit is different measured in different directions transversely to the middle axis of the 2D array 29. The focus can then be displaced more greatly transversely to the middle axis M in that direction in which more ultrasound transducer elements are present per length unit.

This is clear with reference to FIGS. 7 and 9. Whereas, namely, no conditions deviating from the embodiment according to FIGS. 5 and 6 derive for the plane shown in FIG. 8, more ultrasound transducer elements per length unit are present in the plane determinant for FIG. 9 as a consequence of the subdivision of the ultrasound transducer elements, so that a greater displaceability of the focus zone derives transversely to the middle axis M (see the positions of the focus zone $F_5$ and $F_6$ in FIG. 9). In the exemplary embodiment according to FIGS. 7 through 9, thus, the focus zone is displaceable within a region whose shape essentially corresponds to that of an ellipsoid (not rotational-symmetrical) with three principal axes of different length.

Figure 10:
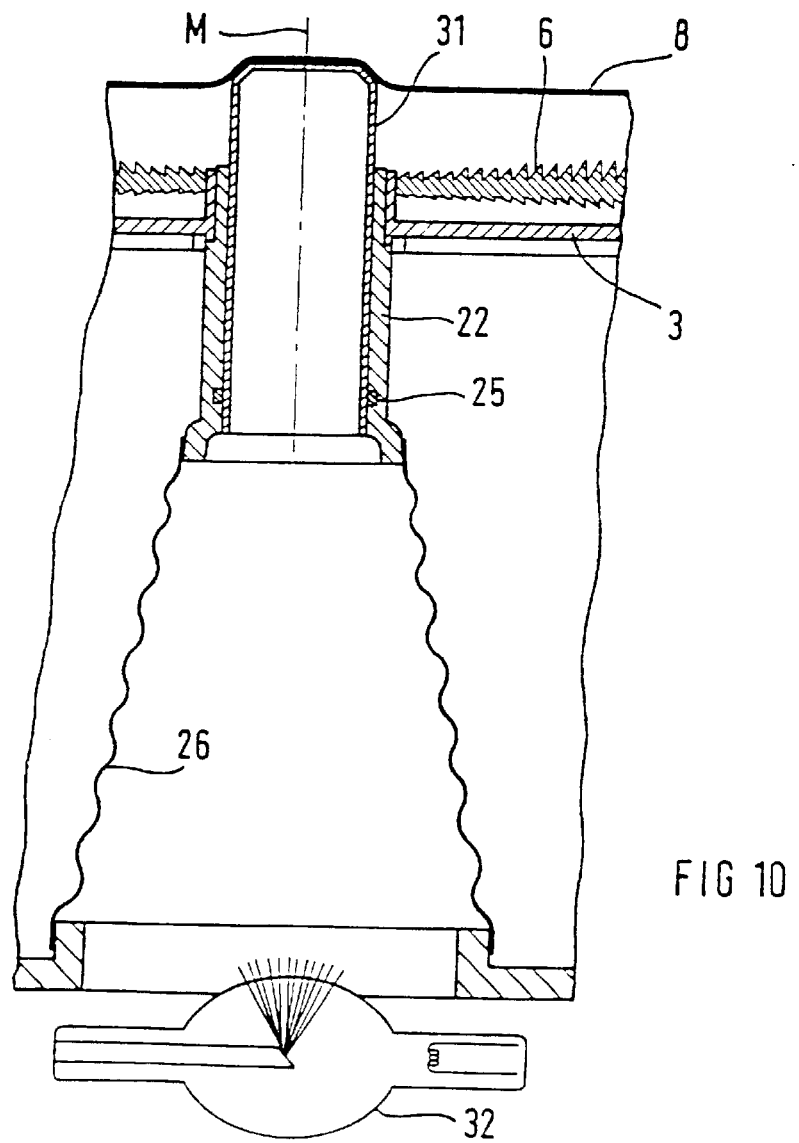
FIG. 10 shows relevant portions of another embodiment of the invention, partly in section.

As a result of the annular shape of the carrier 3 and of the positive lens 6, the ultrasound source 1 of the inventive therapy apparatus comprises an opening 30 that forms an X-ray-transparent region into which an X-ray-transparent tube 31 can be introduced instead of the diagnostic ultrasound applicator 23 in the way illustrated in FIG. 10, so that there is the possibility of locating a region to be treated on the basis of an X-ray diagnostics means whose beam path proceeds through the X-ray-transparent region. Only the X-ray tube 32 of the X-ray diagnostics means is schematically indicated in FIG. 10; it is self-evident that a radiation receiver not shown in FIG. 10 must be present, for example a X-ray image intensifier.

Figure 11:
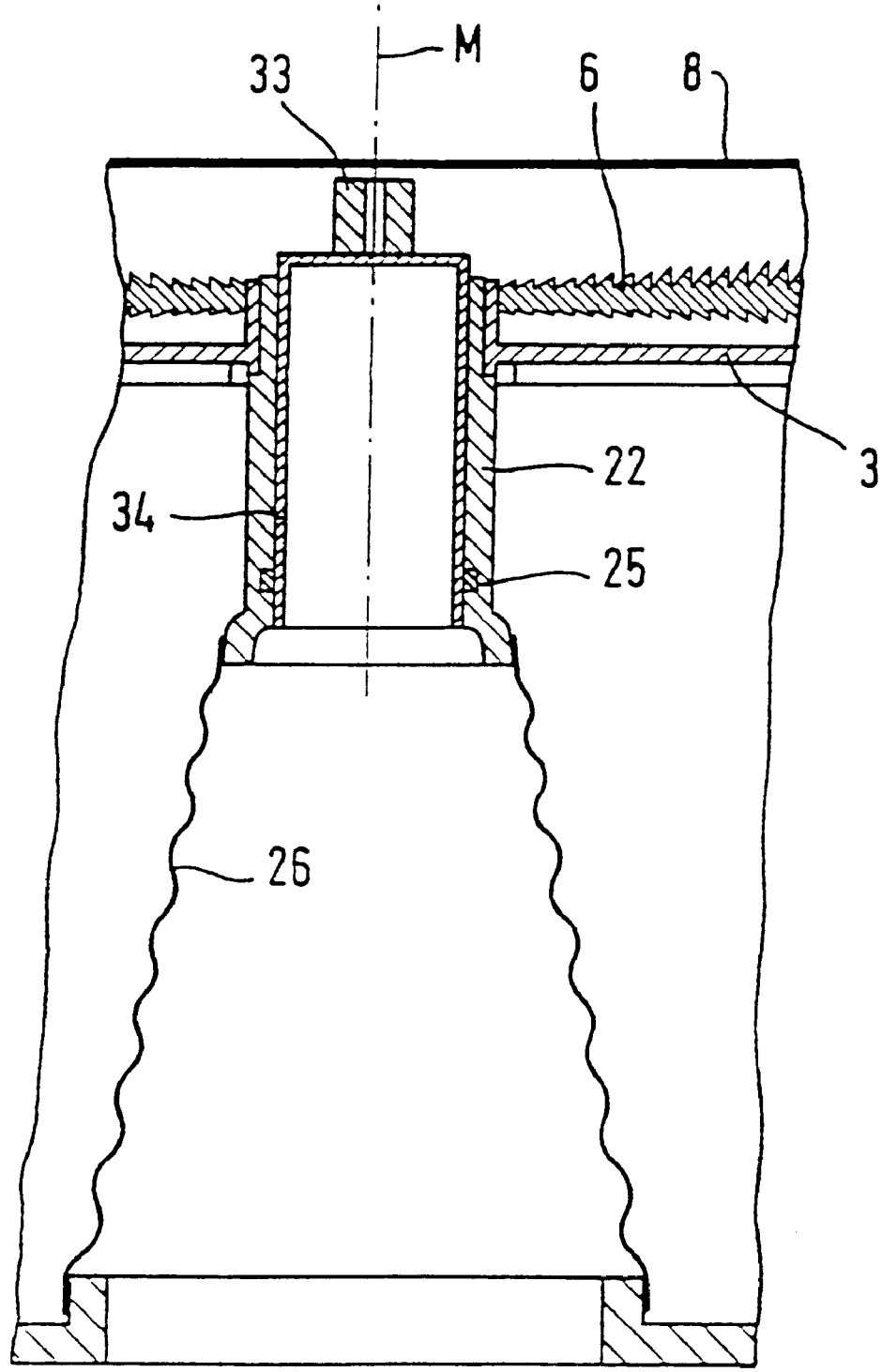
FIG. 11, shows relevant portions of a further embodiment of the invention, partly in section.

According to FIG. 11, there is also the possibility of introducing a MR marker into the opening instead of the ultrasound applicator 23 or, respectively, the tube 31. The MR marker 33 is a plastic cylinder or cone with central bore that is attached to a marker carrier tube 34. Given employment of the inventive therapy apparatus with a MR apparatus, it is thus possible to unambiguously determined the spatial position of therapy the apparatus and appertaining therapy focus with reference to the diagnostic image of the MR apparatus. The plastic produces only low MR contrast compared to the liquid in the bore and around the plastic part. The bore marks the middle axis of the ultrasound source 1. MR-compatible materials are employed for the materials of the therapy apparatus if it is provided for employment with a MR apparatus.

A Fresnel lens is provided as acoustic lens in all described exemplary embodiments. However, a conventional acoustic lens can also be employed instead.

The ultrasound sources of all described exemplary embodiments comprise a central opening into which a diagnostic ultrasound applicator, an X-ray-transparent tube or a MR marker can be partially introduced. Within the scope of the invention, however, the ultrasound source can also be implemented without central opening. An X-ray-transparent region can thereby be nonetheless present, insofar as the ultrasound source exhibits the required transparency at least in the relevant region, whether on the basis of a correspondingly slight thickness of the component parts present there or on the basis of a corresponding selection of material.

A cardanic suspension of the ultrasound source is not required in those exemplary embodiments that contain an ultrasound source executed as 2D array, since the focus zone can also be spatially displaced without this measure. When, however, the displaceability of the focus zone established by the fashioning of the ultrasound source as 2D array is insufficient, there is also the possibility of the cardanic suspension in such ultrasound sources.

Measures, moreover, can also be undertaken that allow a fluid other than the fluid otherwise present in the housing 7 to be provided in the space located between the positive lens 6 and the carrier 3. When the two fluids differ in terms of their critical acoustic properties, however, this must be taken into consideration in the design of the positive lens 6.

I claim as my invention:

1. A therapy apparatus for treatment with focused ultrasound, comprising:
    an ultrasound source comprising a base plate and a plurality of ultrasound transducer elements disposed on a first side of said base plate, said ultrasound transducer elements respectively emitting ultrasound;
    an acoustic lens disposed in a propagation path of said ultrasound emitted by said ultrasound transducer elements for focusing said ultrasound, said base plate being composed of material having a thermal conductivity of at least 10 W (WPK) and having a thickness equal to an odd-numbered multiple of a quarter of a wavelength of said ultrasound in said material of said base plate and having an acoustic impedance of approximately $10^7$ kg/(m$^2$s);
    an ultrasound-conductive coolant disposed at a second, opposite side of said base plate facing toward said acoustic lens, said ultrasound-conductive coolant being contained between said acoustic lens and said base plate; and
    means for operating said ultrasound source as a phased array.

2. A therapy apparatus as claimed in claim 1 wherein said ultrasound-conductive coolant is disposed in a space between said acoustic lens and said base plate, and wherein said therapy apparatus further comprises means for causing said ultrasound-conductive coolant to flow through said space.

3. A therapy apparatus as claimed in claim 2 comprising a circulation path between said space and said means for causing said ultrasound-conductive coolant to flow through said space, and said therapy apparatus further comprising a cooling unit disposed in said circulation path.

4. A therapy apparatus as claimed in claim 1 wherein said means for operating said ultrasound source comprises means for operating said ultrasound source for generating periodic ultrasound, and wherein said acoustic lens comprises a Fresnel lens.

5. A therapy apparatus as claimed in claim 4 wherein said ultrasound transducer elements comprise annular ultrasound transducer elements arranged in an annular array.

6. A therapy apparatus as claimed in claim 5 wherein said Fresnel lens has a plurality of annular zones, and wherein said annular transducer elements are respectively disposed congruently with said annular zones of said Fresnel lens.

7. A therapy apparatus as claimed in claim 6 wherein each of said annular transducer elements has a substantially identical area.

8. A therapy apparatus as claimed in claim 1 wherein said transducer elements are arranged as a two-dimensional array.

9. A therapy apparatus as claimed in claim 8 wherein said two-dimensional array has a middle axis and wherein a number of ultrasound transducer elements per unit length in said two-dimensional array differs along different directions transversely to said middle axis.

10. A therapy apparatus as claimed in claim 1 wherein said ultrasound transducer elements comprise a linear array having a longitudinal axis, and wherein said therapy apparatus comprises means for pivoting said linear array around said longitudinal axis or an axis substantially parallel thereto.

11. A therapy apparatus as claimed in claim 1 wherein said ultrasound transducer elements comprise a linear array having a longitudinal axis, and wherein said therapy apparatus comprises means for adjusting said linear array substantially transversely to said longitudinal axis.

12. A therapy apparatus as claimed in claim 1 further comprising means for cardanically suspending said ultrasound source and said acoustic lens in common for cardonically swivelling said ultrasound source and said acoustic lens.

13. A therapy apparatus as claimed in claim 1 further comprising ultrasound locating means for identifying a site to be treated with said ultrasound.

14. A therapy apparatus as claimed in claim 13 wherein said ultrasound locating means comprises a diagnostic ultrasound transducer.

15. A therapy apparatus as claimed in claim 14 wherein at least one of said acoustic lens and said ultrasound source has an opening therein, and wherein said diagnostic ultrasound transducer projects through said opening.

16. A therapy apparatus as claimed in claim 1 wherein each of said ultrasound source and said acoustic lens has an x-ray transparent region, the respective x-ray transparent regions in said ultrasound source and said acoustic lens being substantially congruent.

17. A therapy apparatus as claimed in claim 1 wherein said ultrasound source has an opening therein, and said therapy apparatus further comprising an insertable element selected from the group consisting of a diagnostic ultrasound transducer and an x-ray transparent tube, said insertable element being introducible into said opening in said ultrasound source.

18. A therapy apparatus as claimed in claim 17 wherein said acoustic lens has an opening therein substantially congruent with said opening in said ultrasound source.

* * * * *